United States Patent [19]

Ramanujam et al.

[11] Patent Number: 5,623,932

[45] Date of Patent: Apr. 29, 1997

[54] DIAGNOSIS OF DYSPLASIA USING LASER INDUCED FLUORESCENCE

[75] Inventors: Nirmala Ramanujam; Anita Mahadevan; Rebecca R. Richards-Kortum, all of Austin; Michele F. Mitchell; Sharon Thomsen, both of Houston, all of Tex.

[73] Assignee: Board of Regents, The University of Texas System, Austin, Tex.

[21] Appl. No.: 469,396

[22] Filed: Jun. 6, 1995

Related U.S. Application Data

[63] Continuation of Ser. No. 60,432, May 12, 1993, Pat. No. 5,421,339.

[51] Int. Cl.$^6$ ............................................. A61B 6/00
[52] U.S. Cl. ............................................. 128/665
[58] Field of Search .................... 128/633, 634, 128/664, 665, 653.1; 607/88–93; 606/3, 14–16; 436/63, 64, 172

[56] References Cited

U.S. PATENT DOCUMENTS 5,348,018  9/1994  Alfano et al. ........................ 128/665
5,408,996  4/1995  Salb ................................... 128/665 X
5,421,339  6/1995  Ramanujam et al. ................ 128/665

Primary Examiner—Ruth S. Smith
Attorney, Agent, or Firm—Arnold, White & Durkee

[57] ABSTRACT

Apparatus and in vivo methods to distinguish normal and abnormal cervical tissue and to detect cervical intraepithelial neoplasia (CIN) in a diagnostic cervical tissue sample. Induced fluorescence intensity spectra from known normal cervical tissue and a diagnostic tissue sample are obtained from the same patient. Peak fluorescence intensity values for normal tissue samples are averaged, as are slope measurements from predetermined portions of spectra induced in both known normal cervical tissue and the diagnostic tissue sample. Peak fluorescence intensities of diagnostic tissue spectra are divided by average peak fluorescence intensity values for normal tissue in the same patient to yield relative peak fluorescence intensity values. Normal and abnormal cervical tissues are distinguished using a predetermined empirical discriminant function of slope measurements derived from normal tissue spectra and relative peak fluorescence intensity measurements in the same patient. CIN is distinguished from tissue with human papilloma virus infection or inflammation using a predetermined empirical discriminant function of average slope measurements on spectra from known normal tissue and slope measurements on a diagnostic tissue spectrum.

11 Claims, 10 Drawing Sheets

DIAGNOSIS OF DYSPLASIA USING LASER INDUCED FLUORESCENCE

This is a continuation of application Ser. No. 08/060,432, filed May 12, 1993 now U.S. Pat. No. 5,421,339.

BACKGROUND OF THE INVENTION

Field of the Invention

The invention relates to methods and apparatus to differentiate between histologically normal and histologically abnormal tissues, and to differentiate neoplastic tissue from histologically abnormal non-neoplastic tissue.

Screening for Cervical Intraepithelial Neoplasia (CIN)

Although there has been a significant decline in the incidence and mortality of invasive cervical carcinoma over the last 50 years, there has been an increase in both the reported and actual incidence of CIN. As a result, it has been estimated that the mortality of cervical carcinoma may rise by 20% in the years 2000–2004 unless screening techniques for CIN are improved.

Present screening for CIN and cervical cancer is relatively inexpensive but labor intensive because it initially relies on the results of a Pap smear; a false negative error rate of 20–30% is associated with insufficient cell sampling and/or inexpert reading of Pap smears. , Given an abnormal Pap smear, colposcopic examination of the cervix (with a magnifying lens) followed by colposcopically directed biopsy and histologic examination of the tissue sample can provide a diagnosis of CIN. Histologic confirmation of the diagnosis, while relatively time-consuming and expensive, is necessary because the accuracy of classification among abnormal tissues by colposcopy alone is limited, even in experienced hands.

Improving the predictive value of colposcopy in distinguishing CIN from other abnormal tissues (e.g., tissue infected with human papilloma virus (HPV) or inflammatory tissue) could reduce the required number of biopsies and thereby increase the speed and efficiency of the screening process. Diagnosis and treatment might be combined in a single office visit, with colposcopically directed treatments including loop electrosurgical procedures (LEEP), cryo and laser therapies, and chemopreventive agents. Further, explication of improved methods to classify tissue as normal or abnormal, while not leading directly to a diagnosis of CIN, would reduce costs by allowing performance of colposcopy by medical technicians less skilled than trained colposcopists (usually physicians).

Spectroscopic Methods in Colposcopy

Spectroscopic methods for differentiating cervical neoplasia from normal cervical tissue in vivo have been described. The methods rely generally on observations that the fluorescence of abnormal tissue is significantly weaker than that of normal tissue at several excitation wavelengths, e.g., 330, 350 and 450 nm. This property has been used for spectroscopic identification of histologically abnormal tissue. For example, in vitro fluorescence intensity comparisons at an excitation wavelength of 330 nm yielded positive predictive value, sensitivity and specificity of 86%, 88% and 75% respectively on colposcopically normal and abnormal biopsies from the same patient. Differences between neoplastic (CIN) and non-neoplastic abnormal tissues (intimation and HPV infection) yielded the largest spectroscopic differences at an excitation wavelength of 330 nm.

Additionally, fluorescence spectra have been measured in vivo to detect neoplastic tissues in different organ systems. A variety of methods for making such determinations have been proposed. For example, ratios of autofluorescence intensity at two different emission wavelengths have been used by many groups, and scores based on multi-variate linear or non-linear regressions and fits to extract concentrations of various chromophores have been proposed by many others for inclusion in decision criteria.

In one application, 337 nm wavelength excitation was applied to colonic tissue. Multi-variate linear regression analysis was used to correctly distinguish adenomatous polyps from normal colon and hyperplastic polyps with positive predictive value, sensitivity and specificity of 86%, 86% and 80% respectively.

Tissue Classification Methods

Previous attempts to reliably distinguish CIN from intimation or HPV infection in vivo using colposcopy alone have been unsuccessful. Fluorescence intensity may be useful in this regard, but is not sufficient in itself because analogous fluorescence intensity measurements of the same tissue type may vary by more than a factor of two from patient to patient, and by about 15% within the same patient. Methods relating fluorescence intensities from abnormal and normal tissues of the same patient, however, tend to be more predictable and therefore more diagnostically useful.

Thus, in general, each patient must serve as her own control. Considering cervical tissues in a given patient excited with 337 nm wavelength electromagnetic excitation, tissues with HPV infection are less fluorescent with than tissues with chronic inflammation, and tissues with dysplastic changes exhibit even lower fluorescence than those with HPV infection. The lowest level of fluorescence (relative to analogous fluorescence measurements on other tissue types in the same patient) is exhibited by tissues with the most abnormal form of CIN. Analogous relationships among tissue fluorescence intensity measurements in a patient may exist if excitation wavelengths other than 337 nm are used because the shape and intensity of cervical tissue spectra do not change substantially when the excitation wavelength is increased or decreased by less than 10 nm.

Additional information useful for tissue classification may be found in the peak emission wavelength of tissues with CIN, which is positively correlated with the peak emission wavelengths of normal tissue spectra from the same patient. This relationship, however, is not observed for tissue samples with inflammation or HPV infection.

Thus, a reliable method to spectroscopically classify tissue as normal or abnormal, and in the latter case to distinguish inflammation or HPV infection from CIN, is needed. Such a method could rely on one or more of the relationships described above, augmented with additional information indicative of the particular separation or classification desired.

SUMMARY OF THE INVENTION

The present invention includes in vivo spectroscopic methods and apparatus for differentiating normal tissue from abnormal tissue and for diagnosing CIN in diagnostic cervical tissue samples. Diagnostic cervical tissue samples are the tissue samples to be evaluated by the non-invasive methods of the present invention. The methods include analysis of tissue fluorescence intensity spectra or portions thereof from both histologically normal tissue and histologically abnormal tissue in a patient desiring diagnosis.

Reference in this application to histologically normal cervical tissue samples in a patient subject to the diagnostic methods of the present invention refers to tissue which is presumptively histologically normal. Normal tissue samples in such subjects are selected in vivo and tested noninvasively as described herein to ensure a substantial likelihood that they actually represent tissue which, if histologically evaluated, would be classified normal.

In certain preferred embodiments, the spectra are represented on two-dimensional plots with fluorescence intensity being represented on the vertical axis and wavelength on the horizontal axis. For calculations involving slope measurements at predetermined wavelengths within spectra having different (unnormalized) peak values, each spectrum is normalized to, its own maximum intensity value. For calculations involving the ratio of the peak intensity of a spectrum from unknown tissue (i.e., from a diagnostic cervical tissue sample) to the peak intensity of a spectrum from (presumptively) normal tissue in the same patient, normalization is not performed.

Detecting Tissue Abnormality

According to the present invention, an in vivo method of detecting tissue abnormality in a diagnostic cervical tissue sample in a patient having known normal cervical tissue comprises illuminating the diagnostic tissue sample and normal cervical tissue with electromagnetic radiation (preferably about 337 nm wavelength). A plurality of normal fluorescence intensity spectra are detected from the known normal cervical tissue, the spectra being obtained serially or simultaneously, preferably through fiber optics which may be placed at a fixed distance from the cervical tissue. In some embodiments, spectra may be detected through analysis of a cervical image which includes the tissue areas to be sampled.

A peak normal fluorescence intensity value is measured in each said normal fluorescence intensity spectrum, and an average peak normal fluorescence intensity calculated from said peak normal fluorescence intensity values. A fluorescence intensity spectrum is also detected from the diagnostic tissue sample, and a peak fluorescence intensity value measured from said fluorescence intensity spectrum.

A predetermined portion of the fluorescence intensity spectrum (preferably in the region corresponding to wavelengths between about 410 nm and about 430 nm) from the diagnostic tissue sample furnishes slope information for calculation of a slope parameter which is indicative of tissue abnormality. The predetermined portion is empirically identified in prior clinical trials as facilitating accurate classification of tissue, and the slope parameter is preferably a function of average slope in the predetermined portion. Each spectrum is preferably normalized to its own maximum value prior to calculation of the slope parameter.

Relative peak fluorescence intensity (preferably relative to average peak normal fluorescence intensity) is calculated as a function of said peak fluorescence intensity value, and tissue abnormality is detected as a function of the calculated slope parameter and relative peak fluorescence intensity. The latter function is preferably a predetermined empirical discriminant function obtained from prior clinical trials. The discriminant function may be either linear or nonlinear.

Detecting CIN

According to the present invention, an in vivo method of detecting CIN in a diagnostic cervical tissue sample in a patient having known normal cervical tissue comprises classifying the diagnostic cervical tissue sample as abnormal by a method described herein, followed by illumination of the diagnostic tissue sample and known normal cervical tissue with electromagnetic radiation, preferably of about 337 nm wavelength.

A first fluorescence intensity spectrum from the diagnostic tissue sample is detected, as is a second fluorescence intensity spectrum from the known normal cervical tissue. A first slope parameter which is indicative of CIN in the diagnostic cervical tissue sample is calculated from a predetermined portion of said first fluorescence intensity spectrum (corresponding to wavelengths between about 440 nm and about 460 nm). A second slope parameter which characterizes normal cervical tissue in the patient is calculated from a predetermined portion of said second fluorescence intensity spectrum (corresponding to wavelengths between about 410 nm and about 430 nm). Both first and second slope parameters are preferably calculated after normalization of the respective fluorescence intensity spectra to peak fluorescence intensity values of 1. Additionally, both first and second slope parameters are preferably functions of average slopes in said normalized first and second fluorescence intensity spectra respectively in regions lying substantially between wavelengths corresponding to the respective predetermined portions.

CIN is detected in the diagnostic cervical tissue sample as a function of said first and second slope parameters, the function preferably comprising a predetermined empirical discriminant function which, in some preferred embodiments is linear.

DETAILED DESCRIPTION

Figure 1:
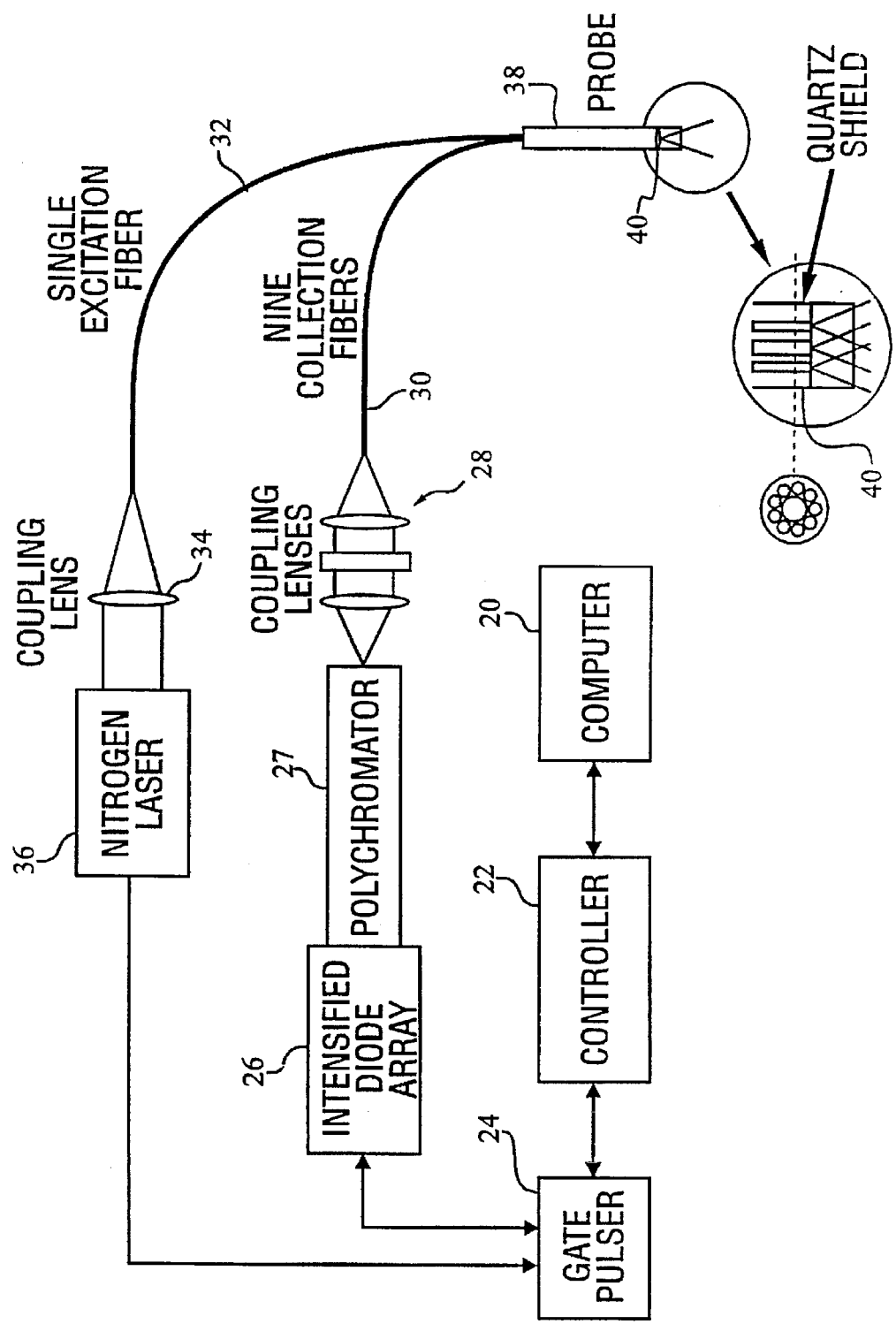
FIG. 1 is a schematic representation of apparatus to classify cervical tissue according to the present invention.

CIN—cervical intraepithelial neoplasia
HPV—human papilloma virus

Normal/Abnormal Tissue Classification

Normal/abnormal tissue classification requires induced fluorescence intensity spectra from tissue areas known to be normal with a sufficiently high probability of accurate classification. Normal and abnormal cervical tissues are primarily identified in vivo by colposcopists In any given patient, it is preferable to collect a plurality of fluorescence intensity spectra from tissue areas identified as normal by a colposcopist. An expected error rate of about 10–20% has been observed, which primarily represents samples which are colposcopically normal but in fact comprise inflammatory tissue. As explained below, provision is made for removal of erroneously-identified normal samples, with the result that those remaining are presumptively normal.

As a patient is examined, peak normal fluorescence intensity values are measured on each spectrum from normal tissue. The intensity values are averaged and a standard deviation of normal peak values calculated. Depending on the degree of confidence required in the screening results and the skill of the operators, a portion of all spectra initially identified as colposcopically normal are discarded (i.e., the spectra are not included in calculation of the average peak normal fluorescence intensity, but may be assigned to the group of spectra to be classified subsequently as normal or abnormal). Criteria for discarding colposcopically normal samples may preferably require discarding all spectra associated with peak values which fall more than one standard deviation below the average peak normal fluorescence intensity.

The peak fluorescence intensity of any test fluorescence spectrum (associated with cervical tissue to be evaluated for normality/abnormality) is divided by the corresponding average normal fluorescence intensity for that patient to yield a relative peak fluorescence intensity for that spectrum. Because normal tissue tends to have relatively high and uniform peak fluorescence intensities in any given patient, the above division will generally result in relative peak fluorescent intensities clustered around a value of approximately 1 for normal tissues. On the other hand, because abnormal tissue (whether characterized as inflammation, HPV infection, or CIN) tends to have lower-than-normal peak fluorescence intensities, the above division will generally result in relative peak fluorescent intensities clustered around a value substantially less than 1 for abnormal tissues. This condition furnishes a partial basis for classifying spectra as representing either normal or abnormal tissue.

A more complete basis for identification of spectra as representing either normal or abnormal tissue is provided by examination of a slope parameter associated with each spectrum, the parameter preferably being derived from slopes measured in the range 400–440 nm, preferably 410–430 nm, and in some preferred embodiments 415–425 nm, as measured on a spectrum normalized to its own peak fluorescence value. The measured slope value is largely governed by two factors, i.e., the peak emission wavelength of fluorophores contributing to the spectrum, and the reabsorption effect of oxy-hemoglobin with an absorption peak at 420 nm. As more hemoglobin contributes, the peak shifts to longer wavelengths and the slope increases. Similarly, as more NADH fluorescence contributes, the peak shifts to longer wavelengths and the slope increases. These effects are observed in diseased tissue, and probably account in part for the capacity of methods of the present invention to differentiate types of diseased tissue on the basis of their induced fluorescence spectra.

The parameter may be an average or tangential slope or other representative value of the range of actual slope values which will in general be found within the specified range (predetermined portion) in any normalized spectrum. Wavelengths defining the extent and location of the predetermined portion of a normalized spectrum which is indicative of tissue abnormality are determined from clinical trials involving fluorescence spectra obtained from tissue with histologically proven diagnoses. That is, the definition of the predetermined portion is empirically derived by comparing slopes over the entire wavelength range to find the portion of that range yielding the best discrimination using the methods described above.

Figure 4:
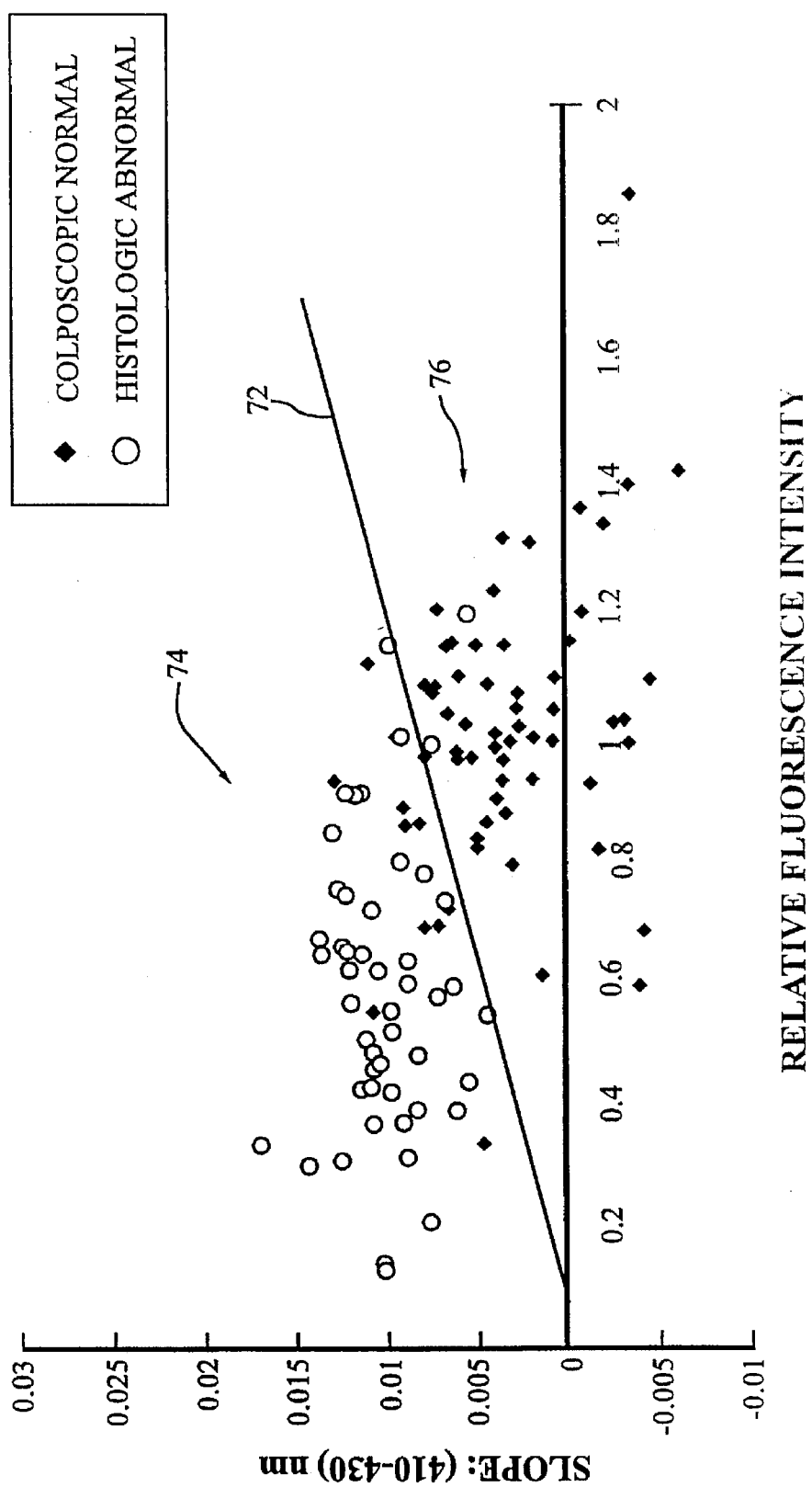
FIG. 4 represents a population of induced fluorescence intensity spectra representing colposcopically normal and histologically abnormal tissue, with a discriminant function for detecting tissue abnormality.

To evaluate a diagnostic cervical tissue sample, a relative peak fluorescence intensity and a slope parameter are calculated as explained above from its induced fluorescence intensity spectrum. The calculated values may then be plotted as a point on the graph of FIG. 4. The line 72 represents a predetermined empirical discriminant function which substantially separates points characterizing colposcopically normal and histologically abnormal tissue. If the point falls below line 72, the tissue sample is diagnosed as normal, whereas if the point falls above line 72, the tissue sample is diagnosed as abnormal. These decision criteria may be implemented mathematically as well as graphically by considering the equation of the line which can be derived from FIG. 4. Note that the position of line 72 (slope and intercept) are subject to change with the addition of more data points from clinical trials to those already present on FIG. 4. Note also, that the position of line 72 may also be expected to change when populations having a substantially different incidence of abnormal cervical tissue from that illustrated in FIG. 4 are considered.

Differentiating CIN From Other Abnormal Tissues

Although normal/abnormal tissue classification on the basis of induced fluorescence spectra is useful for preliminary screening, patients identified as having abnormal cervical tissue must be further evaluated. In particular, CIN should be differentiated from inflammation or HPV infection because of the potential for CIN to progress to invasive cancer.

As an aid to classification, a correlation has been observed between the wavelengths associated with peak intensity in corresponding fluorescence intensity spectra obtained from normal and neoplastic tissue in the same patient. Whereas three sample peak intensity wavelengths of normal spectra in a single patient were observed to be 398, 426 or 442 nm, the corresponding peak intensity wavelengths from CIN spectra in the same patient were observed to be 442, 450 or 460, respectively. Thus, the peak intensity of a fluorescence intensity spectrum tends to occur at longer wavelengths in fluorescence intensity spectra from tissue with CIN, compared to corresponding spectra from normal tissue in the same patient. This wavelength shift is relatively uncommon in abnormal tissues representing HPV infection or inflammation.

Figure 5:
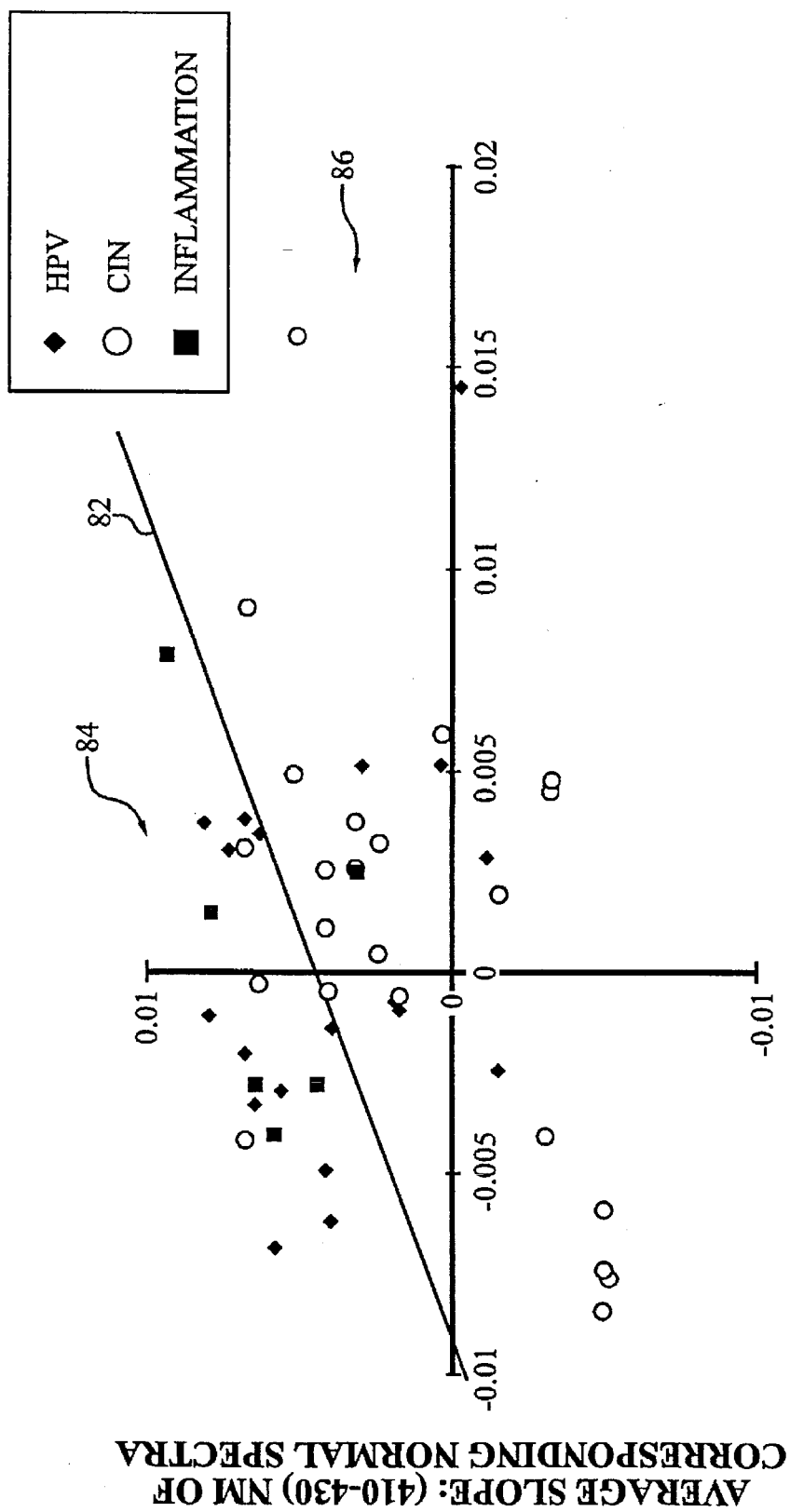
FIG. 5 represents a population of induced fluorescence intensity spectra representing histologically abnormal tissue (i.e., CIN, inflammation, HPV), with a discriminant function for detecting CIN.

A two-dimensional scatter plot was developed to map out the relationship in a population of patients between the peak emission wavelength of the abnormal spectrum and average normal spectra from the same patient. This is shown in FIG. 5, where the abscissa corresponds to the slope of the abnormal spectrum over the wavelength range 440 to 460 nm, and the ordinate represents the average slope of the normal spectra from the same patient over the wavelength range 410–430 nm. All spectra were normalized to a peak intensity of 1 prior to slope calculation. Note that the slope of the spectra from samples with HPV infection or inflammation does not appear to correlate to the average slope of the corresponding normal spectra (linear correlation coefficient=0.072). However, the slope of the spectra from samples with CIN displays a positive correlation (linear correlation coefficient=0.442) to the average slope of the corresponding normal spectra. This enables differentiation of abnormal samples with CIN from those with HPV infection or inflammation. A predetermined empirical discriminant function which allows one to carry out the differentiation for each new patient is represented by the line 82 in FIG. 5, which minimizes the number of misclassified samples.

Thus, CIN tissue spectra are distinguishable from HPV or inflammation tissue spectra on a two-dimensional plot. The horizontal axis of the plot represents the value of a slope parameter obtained from an abnormal spectrum in the wavelength range of about 440 to 460 nm, while the vertical axis represents the value of a slope parameter obtained from a normal spectrum in the same patient in the wavelength range of about 410 to 430 nm.

A predetermined empirical function in two-dimensional space substantially separates points corresponding to CIN tissue fluorescence spectra from points corresponding to HPV or inflammation tissue spectra. In certain preferred embodiments, this function may be linear and acceptably minimize the number of misclassified points. In other preferred embodiments, the function may describe a nonlinear decision surface. Determination of the preferred decision surface for any population depends on the degree to which the population is characterized by clinical data used to estimate the decision surface.

Apparatus for Tissue Classification

FIG. 1 is a schematic representation of apparatus to classify cervical tissue according to the present invention. To obtain tissue fluorescence spectra, electromagnetic radiation (e.g., light, in certain embodiments) in the form of laser light from nitrogen laser 36 is applied through coupling lens 34 and single fiber optic excitation fiber 32 to probe 38. Also within probe 38 are collection fiber optic fibers 30 and quartz shield 40, the shield 40 acting to keep fibers 30 and 32 properly spaced from any surface to which probe 40 is applied, application to a cervix preferably being under colposcopic observation. Resulting tissue fluorescence is transmitted by fibers 30 through coupling lenses 28 to polychromator 27, and thence to intensified diode array 26. Array 26, controlled by controller 22 through gate pulser 24, detects fluorescence intensity spectra which are relayed through controller 22 to computer 20. Computer 20 is programmed to classify tissue in accordance with methods described herein.

Note that laser light is not necessary for practice of the present invention. Laser 36 may be replaced in some embodiments by an incandescent or other type lamp with an associated filter to produce quasi-monochromatic light. Additionally, fibers 32 and 30 may be replaced in some embodiments with fibers serving both the function of illumination (excitation) and transmission of tissue fluorescence. Intensified diode array 26 and polychromator 27 may be replaced by a subassembly comprising radiation filters and photomultiplier tubes to reduce costs in certain embodiments.

Figure 2:
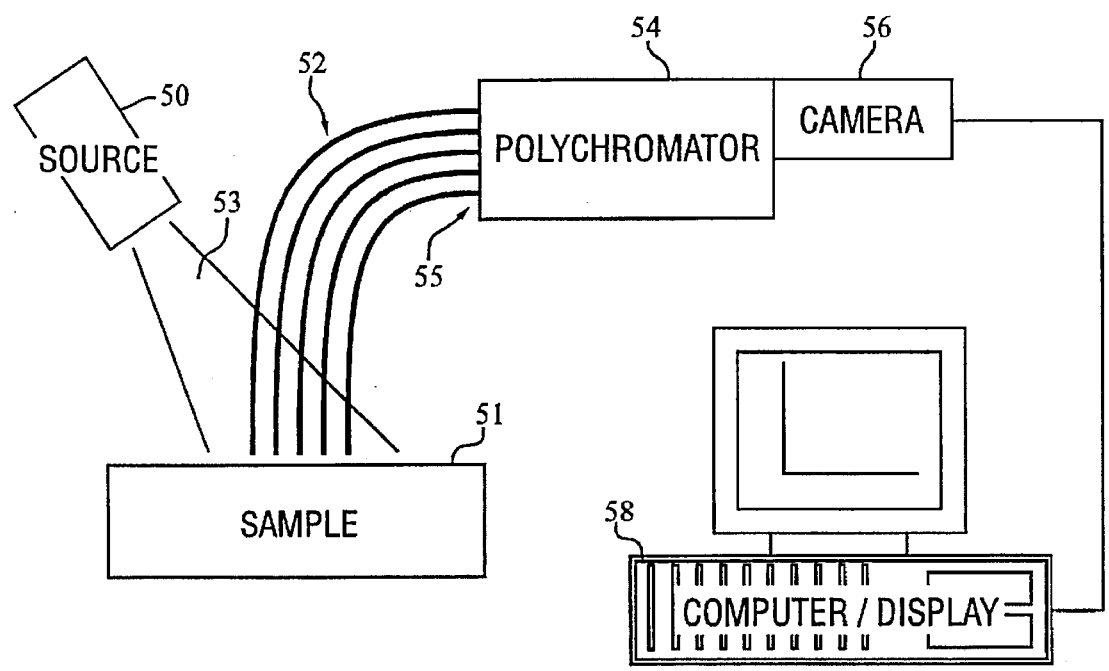
FIG. 2 is a schematic representation of apparatus for multi-pixel spatial-spectral imaging of the cervix.

FIG. 2 schematically illustrates apparatus used in certain embodiments of the present invention to simultaneously collect fluorescence spectra from multiple areas of the cervix. A source 50 of electromagnetic radiation (delivered through fiber or non-fiber optics) is used to illuminate the desired areas of the cervix (sample 51), including both some normal and some abnormal areas. A geometric array 53 of fibers 52 collects tissue fluorescence originating from known normal and unknown regions of the cervix, the latter to be diagnosed. The ends of fibers 52 proximate to imaging polychromator 54 are arranged in a linear array 55 at the entrance slit to polychromator 54. Polychromator 54 is coupled to a charge coupled device camera 56. Polychromator 54 disperses wavelength across one axis of the array, and position on the cervix varies across the other dimension. Thus this system provides a spatial-spectral image on computer-display 58 of fluorescence spectroscopic information in the cervix.

The operator identifies one or more fibers which view normal cervix. The fluorescence intensity spectrum from each fiber viewing an unknown area of the cervix is then processed by the methods described herein to determine whether the tissue is histologically abnormal and whether CIN is present. This information can be presented as a spatial image of tissue histologic condition on computer-display 58.

Figure 3:
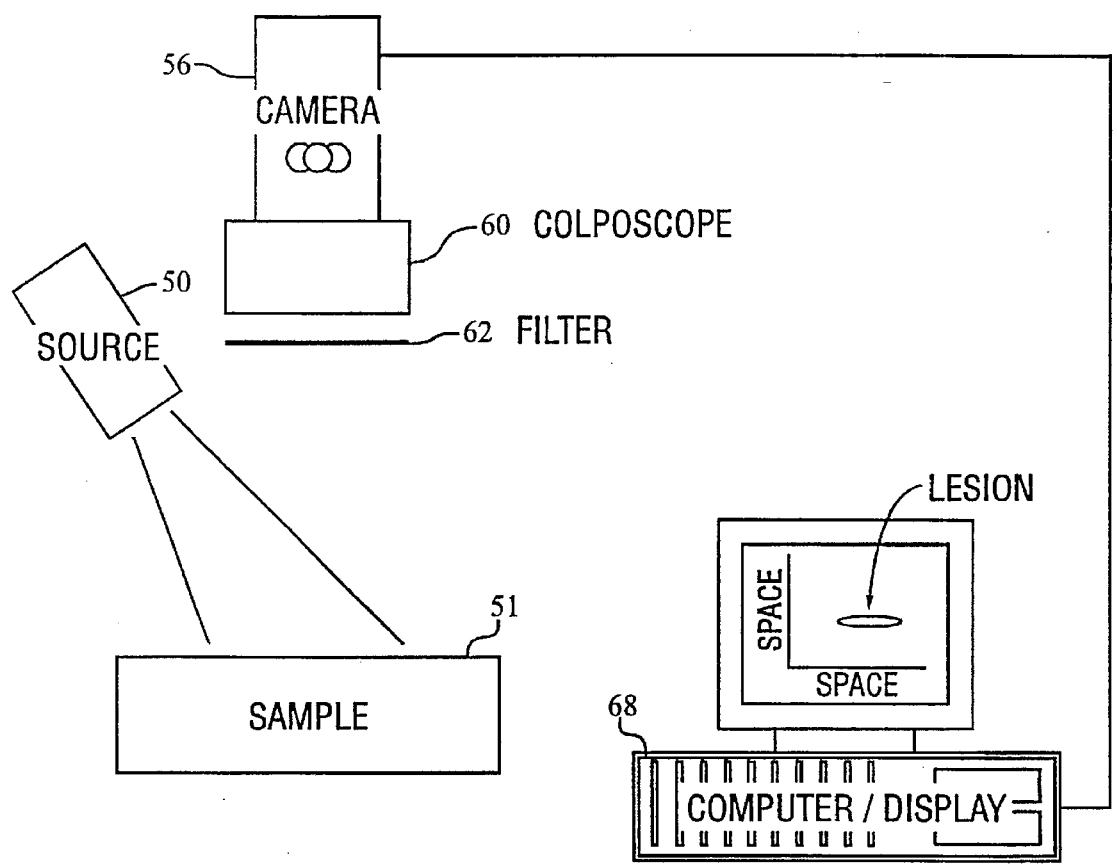
FIG. 3 is a schematic representation of apparatus to acquire and process spectroscopic images of the cervix.

FIG. 3 is a schematic illustration of apparatus for certain embodiments of the present invention. As in FIG. 2, illumination of sample 51 with electromagnetic radiation from source 50 results in fluorescence intensity spectra which are sensed by charge coupled device 56 after passing through variable band pass filter 62 and colposcope imaging optics 60. Computer/display unit 68 accepts spectra from charge coupled device 56 for processing and display.

This system provides a two-dimensional image of variation in fluorescence intensity as a function of position on the cervix at a specific wavelength band governed by the transmission characteristics (optical properties) of imaging optics 60 and filter 62, which can be rapidly changed. Images are acquired at bands centered near 398, 410, 426, 442, 450 and 460 nm sequentially. The maximum intensity $I_{MAX}$ is identified for each pixel. A composite image indicating the peak intensity as a function of position is then formed from these images. Images indicating the slopes of the fluorescence spectra from the tissue in each pixel over the ranges 410–430 nm and 440–460 nm are calculated according to $I(426)-I(410)$ $[(426-410)I_{MAX}]$ and $I(460)-I(442)/[(460-442)I_{MAX}]$. The operator identifies one or more pixels corresponding to normal regions of the cervix. A relative intensity image is constructed by dividing the peak intensity image by the average normal intensity. Thus, for each pixel the relative intensity and slopes at 410–430 nm and 440–460 nm are available. These data are used to classify the state of the tissue in each pixel according to the methods presented herein. This information can be presented on computer-display unit 68 as a spatial image of tissue histologic condition.

Obtaining Decision Surfaces

Data points in FIG. 4 represent induced fluorescence intensity spectra obtained from cervical tissue in a population of patients, each patient having both colposcopically normal tissue and histologically abnormal tissue. The latter tissue includes CIN, inflammatory tissue, and tissue having HPV infection. Note that fluorescence intensities plotted along the abscissa of FIG. 4 are relative to (divided by) average peak normal fluorescence intensity obtained from the population of spectra considered. Spectra from the two tissue groups are processed in accordance with methods described herein to classify the respective tissues as normal or abnormal. Decision surface 72 (a line in 2-space) is empirically established to minimize overlap of substantially normal 76 and substantially abnormal 74 groups. The equation of surface 72 as determined from FIG. 4 constitutes a predetermined discriminant function useful in detecting tissue abnormality in any diagnostic cervical tissue sample when fluorescence intensity spectra are induced in the tissue sample and processed according to methods described herein.

Data points in FIG. 5 represent induced fluorescence intensity spectra obtained from cervical tissue in a population containing histologically abnormal tissue, the latter tissue including CIN, inflammatory tissue, and tissue having HPV infection. Spectra from the three tissue groups are processed in accordance with methods described herein to classify the respective tissues as characteristic of CIN or not characteristic of CIN. Decision surface 82 (a line in 2-space) is empirically established to minimize overlap of substantially CIN 86 and substantially not-CIN 84 groups. The equation of surface 82 as determined from FIG. 5 constitutes a predetermined discriminant function useful in detecting CIN in any histologically abnormal diagnostic cervical tissue sample when fluorescence intensity spectra are induced in the tissue sample and processed according to methods described herein.

Figure 6A:
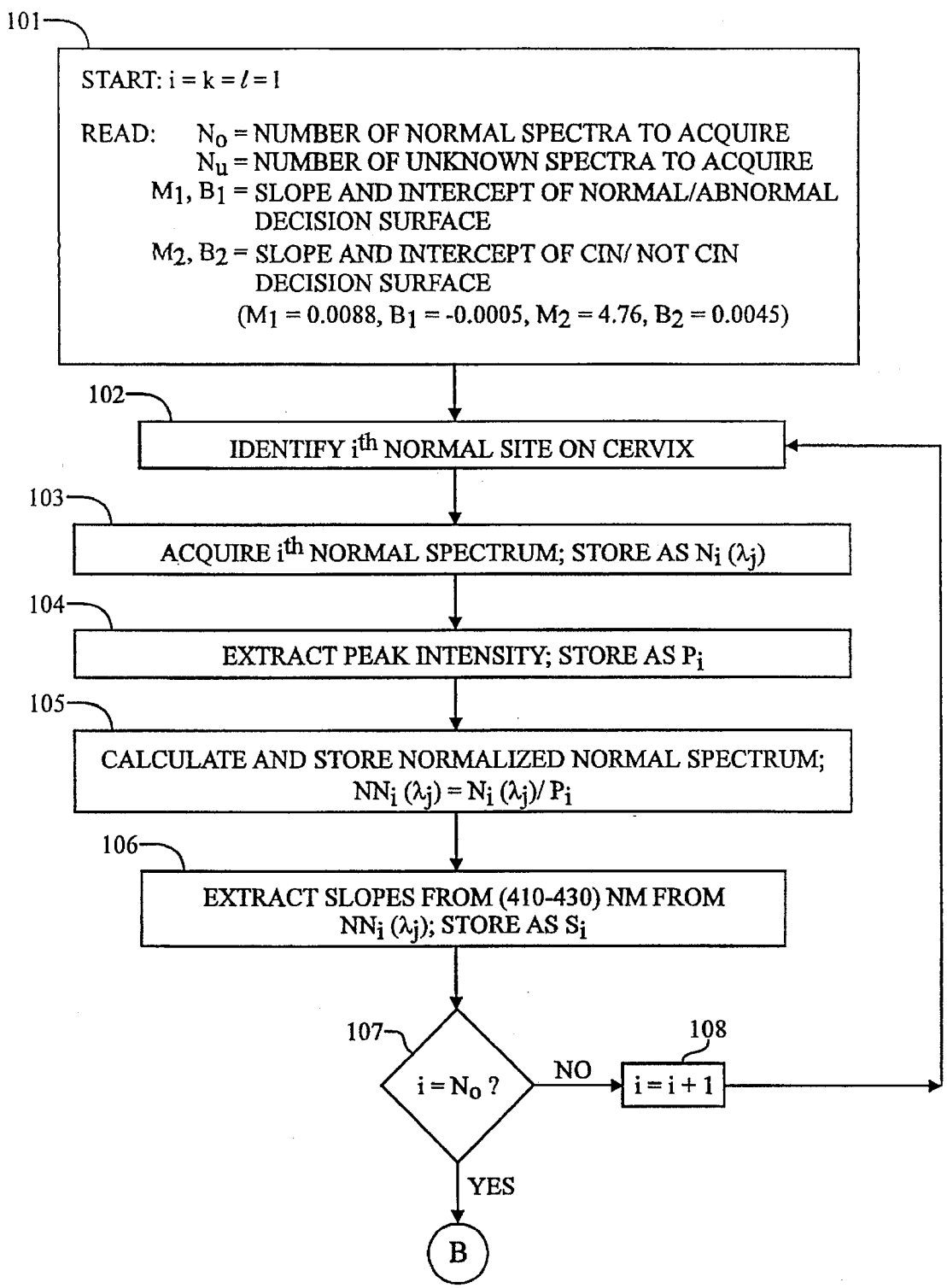
FIGS. 6A–6F illustrate a flow chart to practice preferred embodiments of the methods of the present invention.
Figure 6B:
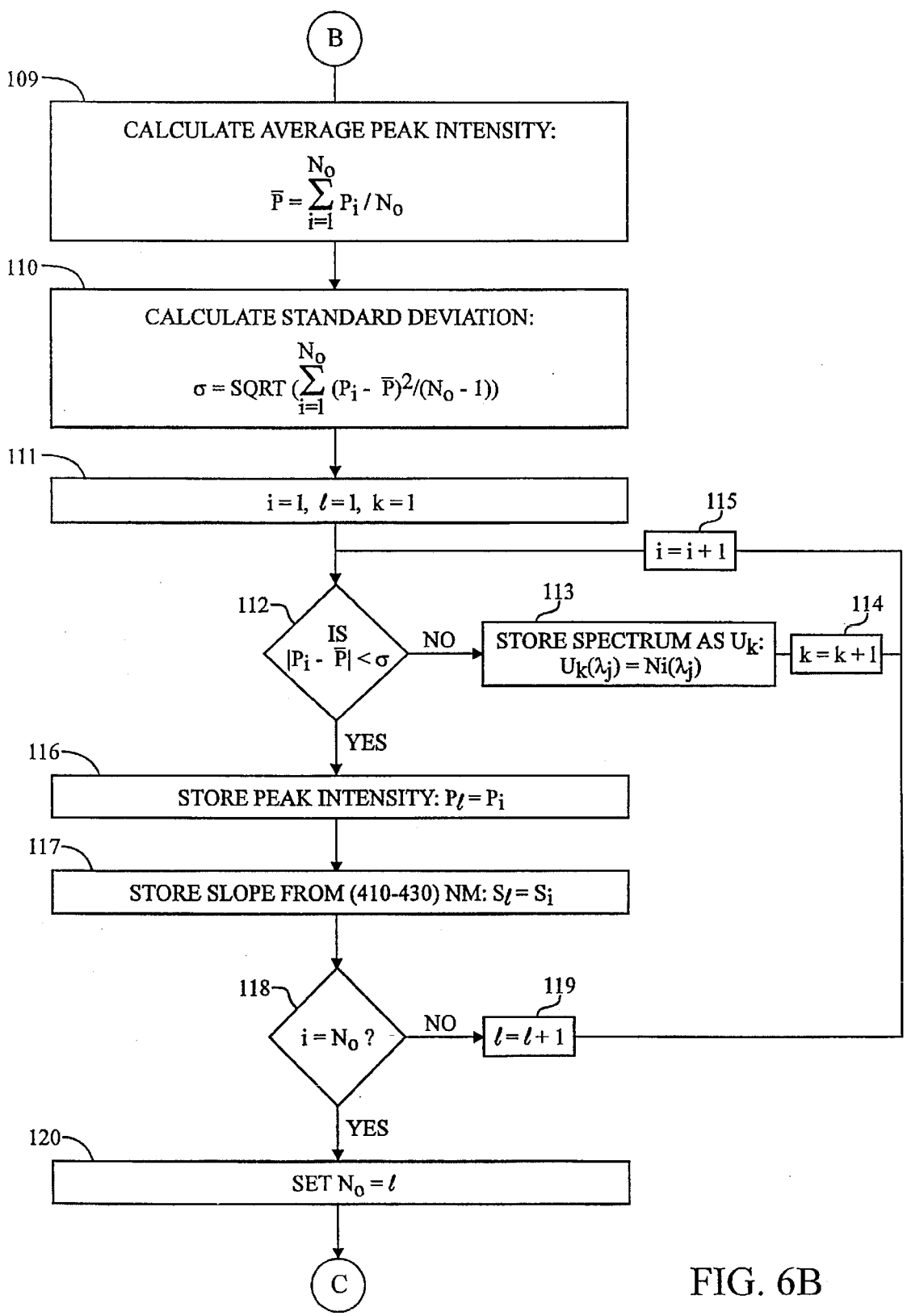
Figure 6C:
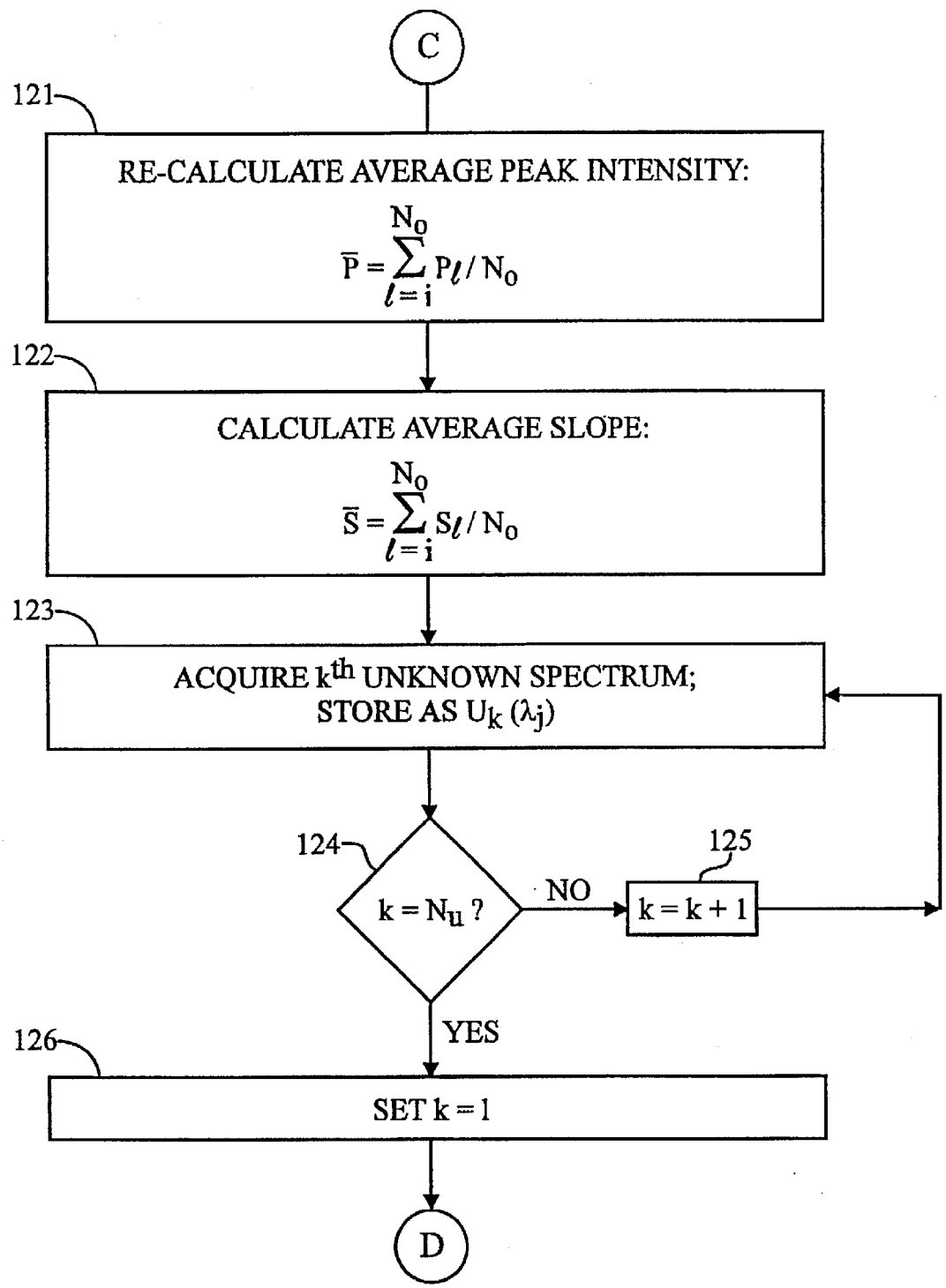
Figure 6D:
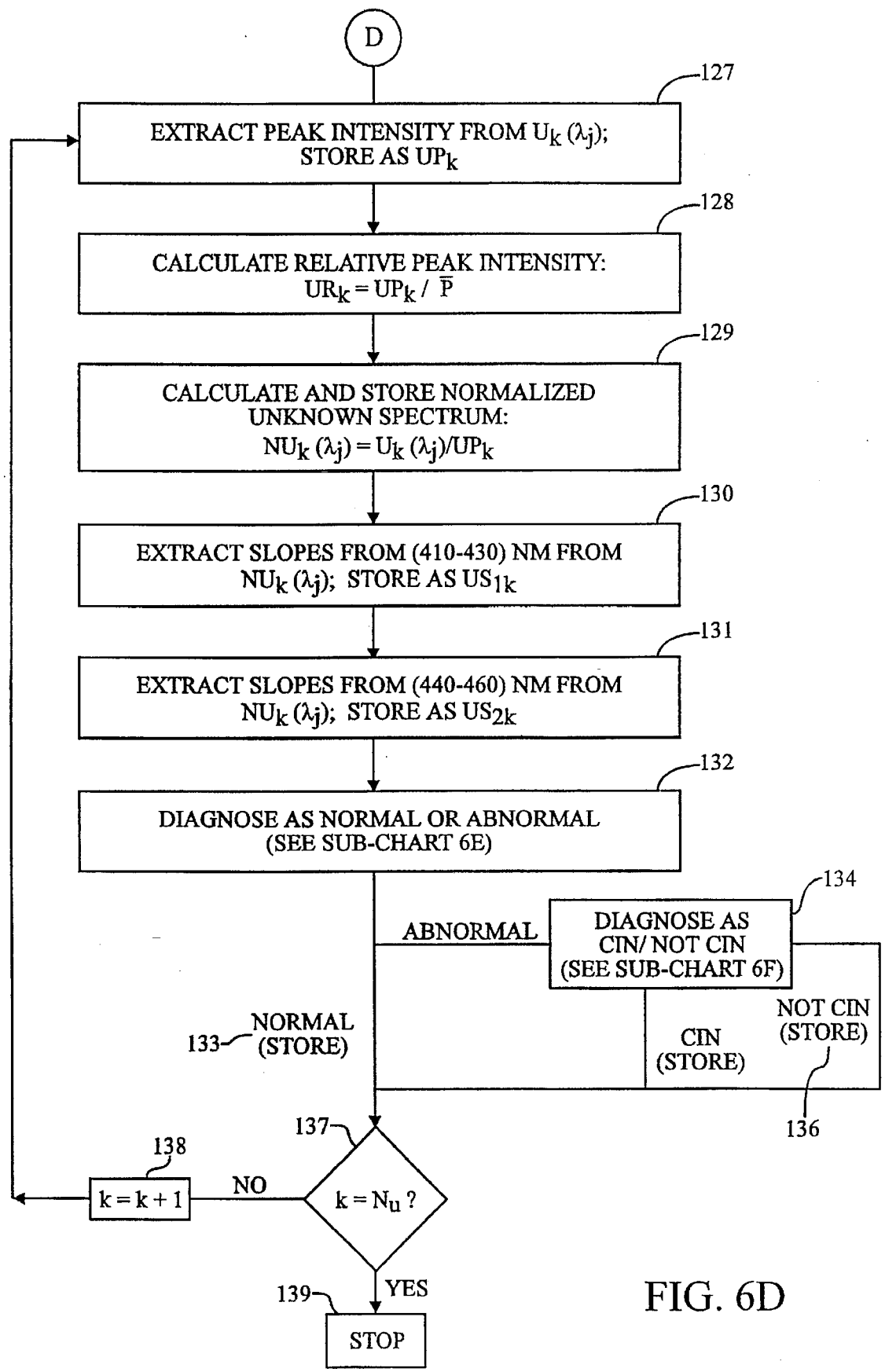
Figure 6E:
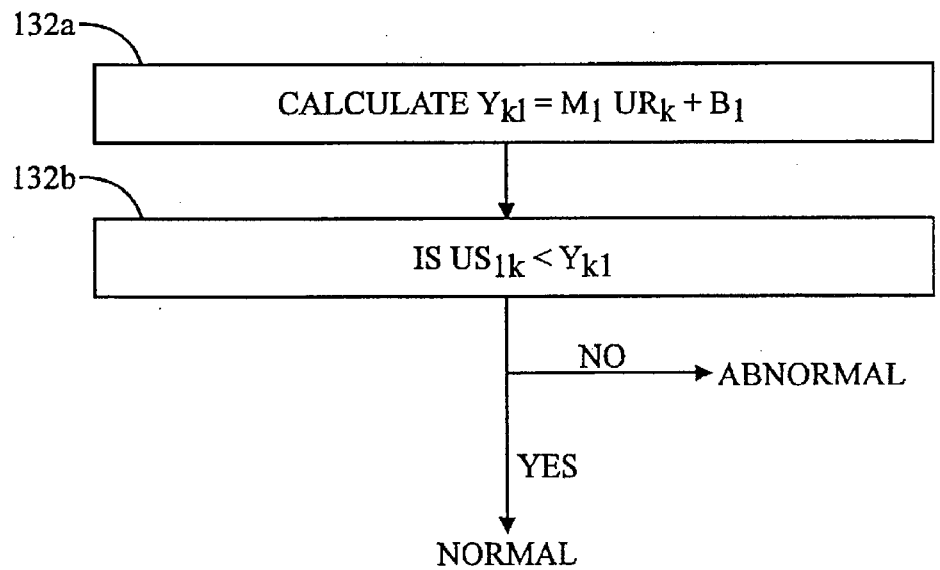
Figure 6F:
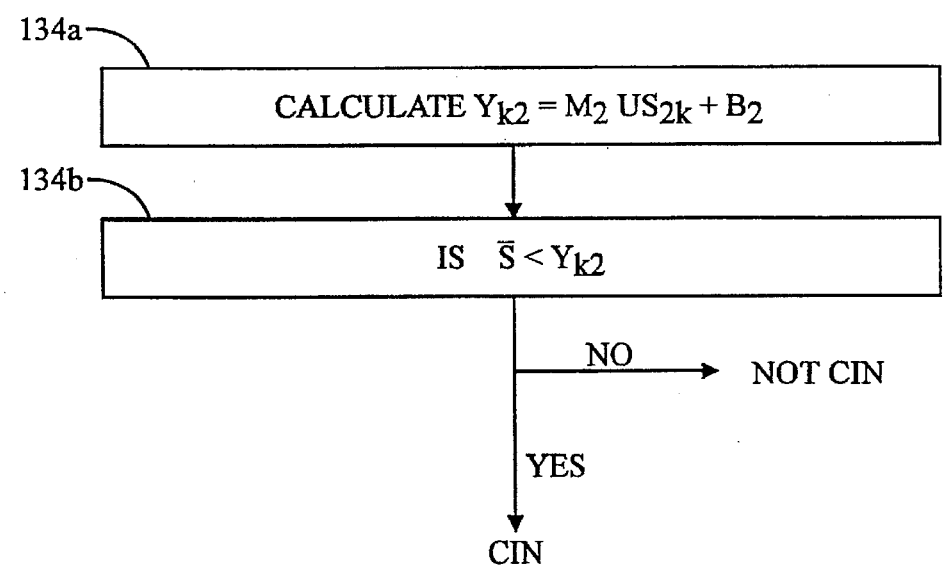

FIGS. 6A–6F illustrate a flow chart to practice preferred embodiments of the methods of the present invention. Note that steps in the flow chart continue from FIG. 6A to FIG. 6B, from FIG. 6B to FIG. 6C, and from FIG. 6C to FIG. 6D. FIGS. 6E and 6F represent subroutines to apply the particular decision rules applicable to either separation of tissue into normal and abnormal classifications (FIG. 6E), or identification of CIN in samples of abnormal tissue (which may include CIN, inflammation or HPV infection) (FIG. 6F). The subroutines (subcharts) illustrated in FIGS. 6E and 6F are called for within the steps illustrated in FIG. 6D. It is assumed in applying the steps called for in FIGS. 6A–6F that sufficient spectra are made available to ensure that normal cervical tissue in the patient is identified and characterized by fluorescence spectra with a sufficiently high likelihood of accurate classification, as indicated in the methods described herein.

What is claimed is:

1. A method for diagnosing dysplasia in cervical tissue, comprising:

subjecting a plurality of cervical tissue sites to electromagnetic energy;

detecting fluorescence in each of the plurality of cervical tissue sites at plural emission wavelengths within a first wavelength range containing peak intensity wavelengths for normal cervical tissue, wherein some of the cervical tissue sites exhibit relatively high and uniform peak fluorescence intensities within the first wavelength range and at least one of the cervical tissue sites does not exhibit relatively high and uniform peak fluorescence intensities within the first wavelength range;

determining a first spectrum characteristic from fluorescence intensities at wavelengths within the first wavelength range for cervical tissue sites exhibiting relatively high and uniform peak fluorescence intensities within the first wavelength range;

detecting fluorescence in the cervical tissue site not exhibiting relatively high and uniform peak fluorescence intensities within the first wavelength range, at plural emission wavelengths within a second wavelength range containing peak intensity wavelengths for a first type of abnormal tissue;

determining a second spectrum characteristic from fluorescence intensities at wavelengths within the second wavelength range for the cervical tissue site not exhibiting relatively high and uniform peak fluorescence intensities within the first wavelength range; and comparing the first spectrum characteristic with the second spectrum characteristic in accordance with a discriminant function, wherein similarity indicates that the cervical tissue site not exhibiting relatively high and uniform peak fluorescence intensities within the first wavelength range contains a first type of abnormal tissue.

2. A method as in claim 1 wherein the first type of abnormal tissue is cervical intraepithelial neoplasia.

3. A method as in claim 2 wherein the discriminant function is a predetermined function that differentiates cervical intraepithelial neoplasia from tissue infected with human papilloma virus and inflamed tissue.

4. A method as in claim 1 wherein the first and second spectrum characteristics are slope parameters.

5. A method as in claim 1 wherein:

the first spectrum characteristic is an average of slopes based on fluorescence intensities obtained in the step of detecting fluorescence within a first wavelength range and normalized to associated peak fluorescence values, and associated with the tissue sites exhibiting relatively high and uniform peak fluorescence intensities within the first wavelength range; and the second spectrum characteristic is a slope based on fluorescence intensities obtained in the step of detecting fluorescence within the second wavelength range.

6. A method as in claim 5 wherein the electromagnetic energy is of a wavelength of about 337 nm and the first wavelength range is about 400–440 nm.

7. A method as in claim 6 wherein the electromagnetic energy is of a wavelength of about 337 nm, the first wavelength range is about 410–430 nm and the second wavelength range is about 440–460 nm.

8. A method as in claim 5 wherein the discriminant function is a predetermined linear empirical function in two-dimensional space.

9. A method as in claim 5 wherein the discriminant function is a predetermined nonlinear empirical function in two-dimensional space.

10. An in vivo method for detecting the presence of CIN tissue in the cervical region of a patient's body, comprising:

irradiating the cervical region with electromagnetic energy;

acquiring a plurality of normal spectra from presumptively normal cervical tissue in the irradiated cervical region;

normalizing the normal spectra, thereby obtaining a normalized normal spectra;

extracting slopes from the normalized normal spectra at wavelengths in a region of peak intensity wavelengths for the normal spectra;

determining an average slope of the slopes extracted from the normalized normal spectra;

determining an average peak intensity of the normalized normal spectra;

acquiring a diagnostic spectrum from diagnostic cervical tissue;

normalizing the diagnostic spectrum, thereby obtaining a normalized diagnostic spectrum;

extracting a slope from the normalized diagnostic spectrum at wavelengths in a region of peak intensity wavelengths for the normal cervical tissue spectra;

extracting a slope from the normalized diagnostic spectrum at wavelengths in a region of peak intensity wavelengths for CIN spectra;

determining a peak intensity of the normalized diagnostic spectrum;

detecting, from the peak intensity of the normalized diagnosis spectrum and the slope extracted from the normalized diagnosis spectrum at wavelengths in a region of peak intensity wavelengths for the normal spectra, abnormal cervical tissue; and differentiating, from the slope extracted from the normalized diagnostic spectrum at wavelengths in a region of peak intensity wavelengths for CIN spectra and from the average slope of the slopes extracted from the normalized normal spectra, abnormal tissue from abnormal tissue that contains CIN.

11. An apparatus for diagnosing dysplasia in cervical tissue, comprising:

means for subjecting a plurality of cervical tissue sites to electromagnetic energy;

means for detecting fluorescence in each of the cervical tissue sites at plural emission wavelengths within a first wavelength range containing peak intensity wavelengths for normal cervical tissue;

means for determining a first spectrum characteristic from fluorescence intensities at wavelengths within the first wavelength range for cervical tissue sites exhibiting relatively high and uniform peak fluorescence intensities within the first wavelength range;

means for detecting fluorescence in a cervical tissue site not exhibiting relatively high and uniform peak fluorescence intensities within the first wavelength range, at plural emission wavelengths within a second wavelength range containing peak intensity wavelengths for a first type of abnormal tissue;

means for determining a second spectrum characteristic from fluorescence intensities at wavelengths within the second wavelength range;

means for comparing the first spectrum characteristic with the second spectrum characteristic in accordance with a discriminant function, wherein similarity indicates that the cervical tissue site not exhibiting relatively high and uniform peak fluorescence intensities within the first wavelength range contains a first type of abnormal tissue; and means for displaying results of the comparing step.

* * * * *

UNITED STATES PATENT AND TRADEMARK OFFICE
CERTIFICATE OF CORRECTION

PATENT NO. : 5,623,932

DATED : April 29, 1997

INVENTOR(S) : Nirmala Ramanujam, Anita Mahadevan, Rebecca R. Richards-Kortum, Michele F. Mitchell and Sharon Thomsen It is certified that error appears in the above-identified patent and that said Letters Patent is hereby corrected as shown below:

On title page, of the patent, in item [56], insert the following items:

--U.S. PATENT DOCUMENTS

| | |
|---|---|
| 5,467,767 6/1995 Ramanujam *et al*. | *128/665* |
| 5,452,723 11/1995 Alfano *et al.* | *128/665* |
| *5,450,,857 9/1995 Wu* et al. | *128/664* |
| *5,421,346 6/1995 Sanyal* | *128/778* |
| 5.421,337 6/1995 Richards-Kortum *et al* | *128/665* |
| 5,419,323 5/1995 Kittrell *et al* | *128/653.*1 |
| 5,408,996 4/1995 Salb | 128/633 |
| 5,348,018 9/1994 Alfano *et al* | *128/665* |
| 5,345,941 9/1994, Rava *et al* | *28/665* |
| 5,318,023 6/1994, Vari *et al.* | 128/633 |
| 5,304,173 4/1994 Kittrell *et al.* | 606/15 |
| 5,290,275, 3/1994 , Kittrell *et al.* | *606/15* |
| 5,280,788, 1/1994, Janes *et al* | *128/665* |
| 5,199,431, 4/1993, Kittrell *et al.* | *128/634* |
| 5,192,278, 3/1993, Hayes *et al.* | *606/15* |
| 5,106,387, 4/1992, Kittrell *et al.* | *606/15* |
| 5,104,392, 4/1992, Kittrell *et al.* | *606/15* |
| 5,092,331, 3/1992, Nakamura *et al.* | *128/634* |
| 5,062,431m 11/1991, Potter | 128/665 |
| 5,038,039, 8/1991, Wong *et al.* | *128/634* |
| 5,036,853, 8/1991, Jeffcoat *et al.* | *128/634* |

UNITED STATES PATENT AND TRADEMARK OFFICE
CERTIFICATE OF CORRECTION

PATENT NO. : 5,623,932

DATED : April 29, 1997

INVENTOR(S) : Nirmala Ramanujam, Anita Mahadevan, Rebecca R. Richards-Kortum, Michele F. Mitchell and Sharon Thomsen It is certified that error appears in the above-identified patent and that said Letters Patent is hereby corrected as shown below:

| | |
|---|---|
| 5,034,010, 7/1991, Kittrell et al. | 606/15 |
| 5,014,707, 5/1991, Schwarz et al. | 128/633 |
| 5,009,655, 4/1991, Daignault, Jr. et al | 606/007 |
| 5,003,977, 4/1991, Suzuki et al. | 128/633 |
| 4,973,848, 11/1990, Kolobanov et al. | 250/458.1 |
| 4,967,745, 11/1990, Hayes et al. | 128/303.1 |
| 4,913,142, 4/1990, Kittrell et al. | 606/7 |
| 4,832,483, 5/1989, Verma | 356/39 |
| 4,755,684, 7/1988, Leiner et al. | 250/461.1 |
| 4,675,529, 6/1987, Kushida | 250/458.1 |
| 4,648,892, 3/1987, Kittrell et al. | 65/4.21 |

PUBLICATIONS

Alfano et al., "Laser Induced Fluorescence Spectroscopy from Native Cancerous and Normal Tissue," *IEEE Journal of Quantum Electronics*, QE-20(12):1507-1511, 1984.

Avrillier et al., "XeCl Excimer Laser-Induced Autofluorescence Spectroscopy for Human Cerebral Tumours Diagnosis: Preliminary Study," *SPIE*, 1894:177-186, 1993.

Bergeron et al., "Complete Fluorescence Spectrum of a Normal and Atherosclerotic Aorta," *Can. J. Phys.*, 66:1035-1039, 1988.

Bosshart et al., "Fluorescence Spectroscopy for Identification of Atherosclerotic Tissue," *Cardiovascular Research*, 26:620-625, 1992.

Bottiroli et al., "Natural Fluorescence of Normal and Neoplastic Human Colon: A Comprehensive "ex vivo" Study," *Lasers in Surgery & Medicine*, 16(1):48-60, 1995

Clarke et al., "Spectroscopic Characterization of Cardiovascular Tissue," Lasers in Surgery and Medicine, 8:45-59, 1988.

UNITED STATES PATENT AND TRADEMARK OFFICE
CERTIFICATE OF CORRECTION

PATENT NO.  :  5,623,932

DATED  :  April 29, 1997

INVENTOR(S)  :  Nirmala Ramanujam, Anita Mahadevan, Rebecca R. Richards-Kortum, Michele F. Mitchell and Sharon Thomsen It is certified that error appears in the above-identified patent and that said Letters Patent is hereby corrected as shown below:

Deckelbaum et al., "Discrimination of Normal and Atherosclerotic Aorta by Laser-Induced Fluorescence," *Lasers in Surgery and Medicine*, 7:330-335, 1987.

Deckelbaum et al., "In-vivo Fluorescence Spectroscopy of Normal and Atherosclerotic Arteries," *SPIE*, 906:314-319, 1988.

D'Hallewin et al., "In Vivo Fluorescence Detection of Human Bladder Carcinoma Without Sensitizing Agents," *Journal of the American Paraplegia Society*, 17(4):161-164, 1994.

Edholm et al., "Tissue Identification During Needle Puncture by Reflection Spectrophotometry," *Biol. Engng.*, 6:409-413, 1968.

Fiarman et al., "Differences in Laser-Induced Autofluorescence between Adenomatous and Hyperplastic Polyps and Normal Confocal Mucosa by Confocal Microscopy," *Digestive Disease & Sciences*, 40(6):11261-1268, 1995.

Fitzmaurice et al., "Argon Ion Laser-Excited Autofluorescence in Normal and Atherosclerotic Aorta and Coronary Arteries: Morphologic Studies," *American Heart Journal*, 118(5)(1):1028-1037, 1989.

Frank et al., "Characterization of Human Breast Biopsy Specimens with Near-IR Raman Spectroscopy," *Anal. Chem.*, 66:319-326, 1994.

Ghadially and Neish, "Porphyrin Fluorescence of Experimentally Produced Squamous Cell Carcinoma," *Nature*, 188:1124, 1960.

Ghadially et al., "Mechanisms Involved in the Production of Red Fluorescence of Human and Experimental Tumours," *Path. Bact.*, 85:77-92, 1963.

Glassman et al., "Excitation Spectroscopy of Malignant and Non-malignant Gynecological Tissues," *Lasers in the Life Sciences*, 6(2):99-106, 1994.

Glassman et al., "Time Resolved and Steady State Fluorescence Spectroscopy from Normal and Malignant Cultured Human Breast Cell Lines," *Lasers in the Life Sciences*, 6(2):91-98, 1994.

Gmitro et al., "Measurement Depth of Laser-Induced Tissue Fluorescence with Application to Laser Angioplasty," *Applied Optics*, 27(9):1844-1849, 1988.

UNITED STATES PATENT AND TRADEMARK OFFICE
CERTIFICATE OF CORRECTION

PATENT NO. : 5,623,932

DATED : April 29, 1997

INVENTOR(S) : Nirmala Ramanujam, Anita Mahadevan, Rebecca R. Richards-Kortum, Michele F. Mitchell and Sharon Thomsen It is certified that error appears in the above-identified patent and that said Letters Patent is hereby corrected as shown below:

Harries et al., "Diagnostic Imaging of the Larynx: Autofluorescence of Laryngeal Tumours Using the Helium-Cadmium Laser," *The Journal of Laryngology and Otology*, 109:108-110, 1995.

Hoyt et al., "Remote Biomedical Spectroscopic Imaging of Human Artery Wall," *Lasers in Surgery and Medicine*, 8:1-9, 1988.

Kittrell et al., "Diagnosis of Fibrous Arterial Atherosclerosis Using Fluorescence," *Applied Optics*, 24(15):2280-2281, 1985.

Kluftinger et al., "Detection of Squamous Cell Cancer and Pre-cancerous Lesions by Imaging of Tissue Autofluorescence in the Hamster Cheek Pouch Model," *Surgical Oncology*, 1:183-188, 1992.

Laifer et al., "Biochemical Basis for the Difference Between Normal and Atherosclerotic Arterial Fluorescence," *Circulation*, 80(6):1893-1901, 1989.

Lam et al., "Detection of Dysplasia and Carcinoma is situ with a Lung Imaging Fluorescence Endoscope Device," *J. Thorac Cardiovasc. Surg.*, 105:1035-1040, 1993.

Leon et al., "Human Arterial Surface Fluorescence: Atherosclerotic Plaque Identification and Effects of Laser Atheroma Ablation," *JACC*, 12(1):94-102, 1988.

Liu et al., "Raman, Fluorescence, and Time-Resolved Light Scattering as Optical Diagnostic Techniques to Separate Diseased and Normal Biomedical Media," *J. Photochem. Photobiol. B: Biol.*, 16:187-209, 1992.

Lohmann et al., "In situ Differentiation Between Nevi and Malignant Melanomas by Fluorescence Measurements," *Naturwissenschaften*, 78:456-457, 1991.

Lohmann et al., "Fluorescence Studies on Lung Tumors," *Z. Naturforsch*, 45c:1063-1066, 1990.

Lohmann and Künzel, "Fluorescence Tomographical Studies on Breast Tissue with Cancer," *Naturwissenschaften*, 77:476-478, 1990.

Lohman, W., "Native Fluorescence of Unstained Cryo-sections of the Skin with Melanomas and Nevi," *Naturwissenschaften*, 76:424-426, 1989.

Mahadevan et al., "Optical Techniques for the Diagnosis of Cervical Precancers: A Comparison of Raman and Fluorescence Spectroscopies," *SPIE*, 2388:110-120, 1995.

UNITED STATES PATENT AND TRADEMARK OFFICE
CERTIFICATE OF CORRECTION

PATENT NO.    :   5,623,932

DATED         :   April 29, 1997

INVENTOR(S)   :   Nirmala Ramanujam, Anita Mahadevan, Rebecca R. Richards-Kortum, Michele F. Mitchell and Sharon Thomsen It is certified that error appears in the above-identified patent and that said Letters Patent is hereby corrected as shown below:

Mahadevan et al., "Study of the Fluorescence Properties of Normal and Neoplastic Human Cervical Tissue," *Lasers in Surgery and Medicine*, 13:647-655, 1993.

Manoharan et al., "Ultraviolet Resonance Raman Spectroscopy for Detection of Colon Cancer," *Lasers in Life Sciences*, 6:217-227, 1995.

Manoharan et al., "Laser-induced Fluorescence Spectroscopy of Colonic Dysplasia: Prospects for Optical Histological Analysis," *SPIE*, 2388:417-421, 1995.

Montán and Strömblad, "Spectral Characterization of Brain Tumors Utilizing Laser-Induced Fluorescence," *Lasers in Life Sciences*, 1(4):275-285, 1987.

Mosier-Boss et al., "Fluorescence Rejection in Raman Spectroscopy by Shifted-Spectra, Edge Detection, and FFT Filtering Techniques," *Applied Spectroscopy*, 49(5):630-638, 1995.

Nishioka, "Laser-Induced Fluorescence Spectroscopy," *Experimental and Investigational Endoscopy*, 4(2):313-326, 1994.

Oraevsky et al., "XeCl Laser-Induced Fluorescence of Atherosclerotic Arteries. Spectral Similarities Between Lipid-Rich Lesions and Peroxidized Lipoproteins," *Circulation Research*, 72:;84-90, 1993.

Ozaki et al., "Biomedical Application of Near-Infrared Fourier Transform Raman Spectroscopy, Part I: The 1064-nm Excited Raman Spectra of Blood and Met Hemoglobin," *Applied Spectroscopy*, 46(3):533-536, 1992.

Palcic et al., "Detection and Localization of Early Lung Cancer by Imaging Techniques," *Chest*, 99:742-743, 1991.

Papazoglou et al., "Laser-Induced Fluorescence Detection of Cardiovascular Atherosclerotic Deposits via Their Natural Emission and Hypocrellin (HA) Probing," *J. Photochem. Photobiol. B: Biol.*, 22:139-144, 1994.

Ramanujam et al., "*In vivo* Diagnosis of Cervical Intraepithelial Neoplasia Using 337-nm-Excited Laser-Induced Fluorescence," *Proc. Natl. Acad. Sci. USA*, 91:10193-10197, 1994.

Ramanujam et al., "Fluorescence Spectroscopy: A Diagnostic Tool for Cervical Intraepithelial Neoplasia (CIN)," *Gynecologic Oncology*, 52:31-38, 1994.

Richards-Kortum et al., "476 nm Excited Laser-Induced Fluorescence Spectroscopy of Human Coronary Arteries: Applications in Cardiology," *American Heart Journal*, 122(4)(1):1141-1150, 1991.

UNITED STATES PATENT AND TRADEMARK OFFICE
CERTIFICATE OF CORRECTION

PATENT NO. : 5,623,932

DATED : April 29, 1997

INVENTOR(S) : Nirmala Ramanujam, Anita Mahadevan, Rebecca R. Richards-Kortum, Michele F. Mitchell and Sharon Thomsen It is certified that error appears in the above-identified patent and that said Letters Patent is hereby corrected as shown below:

Richards-Kortum et al., "Spectral Diagnosis of Atherosclerosis Using an Optical Fiber Laser Catheter," *American Heart Journal*, 118(2):381-391, 1989.

Richards-Kortum et al., "A One-Layer Model of Laser-Induced Fluorescence for Diagnosis of Disease in Human Tissue: Applications to Atherosclerosis," *IEEE Transactions on Biomedical Engineering*, 36(12):1222-1232, 1989.

Richards-Kortum et al., "Survey of the UV and Visible Spectroscopic Properties of Normal and Atherosclerotic Human Artery Using Fluorescence EEMS," In *Optronic Techniques in Diagnostic and Therapeutic Medicine*, ed. R. Pratesi, Plenum, 1991, pp. 129-138.

Richards-Kortum et al., "A Model for Extraction of Diagnostic Information from Laser Induced Fluorescence Spectra of Human Artery Wall," *Spectrochimica Acta*, 45A(1):87-93, 1989.

Römer et al., "Laser-Induced Fluorescence Microscopy of Normal Colon and Dysplasia in Colonic Adenomas: Implications for Spectroscopic Diagnosis," *The American Journal of Gastroenterology,* 90(1):81-87, 1995.

Sartori et al., "Autofluorescence Maps of Atherosclerotic Human Arteries-A New Technique in Medical Imaging, *IEEE Journal of Quantum Electronics*, QE-23(10):1794-1797, 1987.

Schomacker et al., "Ultraviolet Laser-Induced Fluorescence of Colonic Polyps," *Gastroenterology*, 102:1155-1160, 1992.

Sterenborg et al., "In vivo Fluorescence Spectroscopy and Imaging of Human Skin Tumours," *Lasers in Medical Science*, 9:191-201, 1994.

van Gemert et al., "Optical Properties of Human Blood Vessel Wall and Plaque," *Lasers in Surgery and Medicine*, 5:235-237, 1985.

Verbunt et al., "Characterization of Ultraviolet Laser-Induced Autofluorescence of Ceroid Deposits and Other Structures in Atherosclerotic Plaques as a Potential Diagnostic for Laser Angiosurgery," *American Heart Journal*, 123(1):208-216, 1992.

UNITED STATES PATENT AND TRADEMARK OFFICE
CERTIFICATE OF CORRECTION

PATENT NO. : 5,623,932

DATED : April 29, 1997

INVENTOR(S) : Nirmala Ramanujam, Anita Mahadevan, Rebecca R. Richards-Kortum, Michele F. Mitchell and Sharon Thomsen It is certified that error appears in the above-identified patent and that said Letters Patent is hereby corrected as shown below:

Yuanlong et al., "Characteristic Autofluorescence for Cancer Diagnosis and Its Origin," *Lasers in Surgery and Medicine*, 7:528-532, 1987.
Zeng et al., "Autofluorescence Distribution in Skin Tissue Revealed by Micropectrophotometer Measurements," *SPIE*, 1876:129-135, 1993.
Zeng et al., "A Computerized Autofluorescence and Diffuse Reflective Spectroanalyser System for in vivo Studies," *Phys. Med. Biol.*, 38:231-240, 1993.--

Signed and Sealed this

Twenty-fourth Day of March, 1998

*Attest:*

BRUCE LEHMAN

*Attesting Officer*  *Commissioner of Patents and Trademarks*